United States Patent
Hamandi et al.

(10) Patent No.: US 10,561,783 B2
(45) Date of Patent: Feb. 18, 2020

(54) CENTRIFUGAL SEPARATING ASSEMBLY FOR POSITIONING A LAYER OF A FLUID BIOLOGICAL PRODUCT AT A SELECTED LOCATION

(71) Applicants: Ziad Hamandi, Lake Worth, FL (US); Shawn R. Browning, Jupiter, FL (US)

(72) Inventors: Ziad Hamandi, Lake Worth, FL (US); Shawn R. Browning, Jupiter, FL (US)

( * ) Notice: Subject to any disclaimer, the term of this patent is extended or adjusted under 35 U.S.C. 154(b) by 432 days.

(21) Appl. No.: 15/447,991

(22) Filed: Mar. 2, 2017

(65) Prior Publication Data

US 2017/0173255 A1 Jun. 22, 2017

Related U.S. Application Data

(63) Continuation-in-part of application No. 14/159,689, filed on Jan. 21, 2014, now Pat. No. 9,610,590.

(60) Provisional application No. 61/754,207, filed on Jan. 18, 2013.

(51) Int. Cl.
*A61M 1/36* (2006.01)
*B04B 5/04* (2006.01)
*G01N 33/49* (2006.01)
*B01L 3/00* (2006.01)

(52) U.S. Cl.
CPC .......... *A61M 1/3693* (2013.01); *B01L 3/502* (2013.01); *B01L 3/5021* (2013.01); *B04B 5/0407* (2013.01); *B04B 5/0414* (2013.01); *B04B 5/0421* (2013.01); *G01N 33/491* (2013.01); *B01L 2200/026* (2013.01); *B01L 2200/0694* (2013.01); *B01L 2300/028* (2013.01); *B01L 2300/042* (2013.01); *B01L 2300/0854* (2013.01); *B01L 2400/0409* (2013.01)

(58) Field of Classification Search
CPC .... A61M 1/3693; B01L 3/502; B01L 3/5021; B01L 2400/0409; B01L 2300/0854; B01L 2300/042; B01L 2200/0694; B01L 2200/026; B01L 2300/028; B04B 5/0421; B04B 5/0407; B04B 5/0414; G01N 33/491
USPC ........ 73/863; 422/548, 533; 210/360.1, 782, 210/789; 494/16
See application file for complete search history.

(56) References Cited

U.S. PATENT DOCUMENTS

| | | | |
|---|---|---|---|
| 2012/0082652 A1* | 4/2012 | Sengun | A61M 1/029 424/93.72 |
| 2014/0054246 A1* | 2/2014 | Landrigan | A61M 1/3693 210/800 |
| 2015/0104824 A1* | 4/2015 | Walker | B01L 3/5021 435/30 |

* cited by examiner

*Primary Examiner* — Walter D. Griffin
*Assistant Examiner* — Shuyi S. Liu
(74) *Attorney, Agent, or Firm* — The Concept Law Group, PA; Scott D. Smiley; Scott M. Garrett

(57) ABSTRACT

A centrifugal separating assembly for separating a fluid biological product into discrete components by centrifugation is disclosed. The assembly includes a first container defining a first cavity adapted to receive a human biological product, the first container having a circular upper wall, a cylindrical sidewall, and a concave shaped bottom wall. The assembly further includes a second container defining a second cavity adapted to receive discrete components. The first container is positioned within the second container, and moveable to a selected position within the second container so that a layer of a fluid biological product will be at a desired location after centrifugation.

20 Claims, 14 Drawing Sheets

600

600

600

600

800

CENTRIFUGAL SEPARATING ASSEMBLY FOR POSITIONING A LAYER OF A FLUID BIOLOGICAL PRODUCT AT A SELECTED LOCATION

CROSS-REFERENCE TO RELATED APPLICATION

This application is a Continuation-in-part Application, which claims benefit of co-pending U.S. Non-provisional patent application Ser. No. 14/159,689 filed on Jan. 21, 2014, which claims priority to U.S. Provisional Patent Application No. 61/754,207 filed Jan. 18, 2013, the entireties of which are incorporated by reference.

FIELD OF THE INVENTION

The present invention relates generally to a centrifugal separating assembly, and more particularly relates to a centrifugal separating assembly having a first container coupled to a second container, the assembly configured such that heavier particulates travel from the first to the second container when the assembly is rotated in a centrifugal movement.

BACKGROUND OF THE INVENTION

It is sometimes desirable to separate particulates from a solution. It is well-known to use a centrifuge to separate particulates from a solution. As known in the art, a centrifuge is a device driven by a motor that rotates an object about a fixed axis, applying a centrifugal force perpendicular to the axis of rotation to separate an initial solution, or fluid product into discrete components.

Blood is a biological fluid product that can be characterized as a suspension of particles in a fluid. Blood primarily includes plasma, white blood cells, platelets, red blood cells, and other particulates present in different ratios and having different densities. When a blood sample is centrifuged, discrete layers are formed according to their densities. The least dense particulates will separate to form a top layer and the most dense particulates will separate and form a bottom layer. After blood is centrifuged a top layer is formed that is substantially plasma, a bottom layer is formed that is substantially red blood cells, and a middle layer is formed that is known in the art as a "buffy coat." The buffy coat contains white blood cells and platelets with an amount of plasma and red blood cells. It is often desirable to isolate the buffy coat for various applications.

It is sometimes desirable to adjust the ratio of red blood cells present in the buffy coat. However, many prior art devices are configured such that adjusting the ratio of red blood cells in the buffy coat requires several steps and is cumbersome to achieve. Also, many prior art devices are configured such that particulate residue builds on the sidewalls over time, reducing optimization of a desired concentrate.

In the same vein, it is sometimes desirable to adjust the ratio of white blood cells in the buffy coat. White blood cells are the cells of the immune system that aid in protecting against infectious disease and foreign invaders in the human body. More specifically, white blood cells help the body to fight infections by attacking bacteria, viruses, and germs that invade the body. White blood cells are ultimately derived from stem cells in the bone marrow and circulate throughout the bloodstream.

The number of white blood cells present in blood is often an indicator of disease. For example, a number of diseases trigger a response by the immune system and cause an increase in the number of white blood cells, while other conditions may affect the production of white blood cells by the bone marrow or the survival of white blood cells in circulation. As such, one reason that it is desirable to isolate the buffy coat is to evaluate a blood sample in order to monitor diseases and recommend certain treatment protocols based on the white blood cell count. Choosing the appropriate concentration of white blood cells can be an important aspect of a patient's successful recovery.

Unfortunately, known methods of centrifugation result in a buffy coat layer that is minimal in comparison to the overall volume of a blood sample, thus making the buffy coat difficult to analyze. In addition, many prior art methods of centrifugation do not allow a physician to selectively choose the concentration of white blood cells present in the buffy coat layer. In the same vein, such methods of centrifugation do not provide the physician with the ability to selectively alter the presence of stem cells obtained from a bone marrow sample for reintroduction at a patient's injury site. Furthermore, many prior art devices include numerous moving parts that are difficult to operate and which are prone to user error. Therefore, a need exists to overcome the problems with the prior art as discussed above and that reduces residue build-up on the sidewalls, optimizes the concentrate of a desired layer(s), increases fluid exchange efficiency, and provides a more convenient device and method of adjusting ratios of particulates in a desired layer.

SUMMARY OF THE INVENTION

The invention provides a centrifugal separating assembly that overcomes the hereinafore-mentioned disadvantages of the heretofore-known devices and methods of this general type and that separates fluid products into discrete components.

With the foregoing and other objects in view, there is provided, in accordance with the invention, a centrifugal separating assembly for separating a fluid biological product into discrete components by centrifugation, the assembly comprising:
  a first container defining a first cavity adapted to receive and hold the fluid biological product, the first container having:
    a circular upper wall,
    a first cylindrical wall extending downwardly from a circumferential edge of the circular upper wall, and
    a concave shaped bottom wall extending inwardly and downwardly from a circumferential edge of the first cylindrical wall, the concave shaped bottom wall terminating at a distal end of the first container and the distal end of the first container defining a first tubular conduit receiving aperture;
  a second container defining a second cavity adapted to receive discrete components of the fluid biological product during centrifugation, the second container having:
    a convex shaped upper wall extending upwardly and inwardly from an upper circumferential edge of a second cylindrical wall and terminating at a distal end of the second container, the distal end of the second container defining a second tubular conduit receiving aperture,
    the second cylindrical wall extending downwardly from a circumferential edge of the convex shaped upper wall, and a circular bottom wall extending inwardly from a lower circumferential edge of the second cylindrical wall; and a tubular conduit having a first linear length between a first distal end and a second distal end of the tubular conduit, the first and second distal ends being engaged with the first and the second tubular conduit receiving apertures, respectively, defining a fluid impermeable passageway between the first and the second container.

In accordance with another feature, the first container and the second container are made of polycarbonate.

In accordance with a further feature of the present invention, a volume of the second container is adapted to be a predetermined percentage of a volume of the first container.

In accordance with a further feature of the present invention, the second container is removeably attached to the tubular conduit.

In accordance with the present invention, an embodiment of the present invention also includes at least one of a self-sealing port and a valve disposed along the first linear length of the tubular conduit.

In accordance with another feature, an embodiment of the present invention also includes a third container adapted to engage a second linear length of the tubular conduit, the second linear length being substantially perpendicular to the first linear length.

In accordance with yet another feature, the assembly is adapted to rotate in a centrifugal movement where the first container is closest to an imaginary axis of rotation and the second container is distally located along an imaginary pendulum swing arm with reference to the second container, such that the second container will travel a further distance than will the first container during the centrifugal movement.

In accordance with a further feature of the present invention, the fluid biological product is human blood and the second container is sized to hold a volume equal to an anticipated percentage of red blood cells present in the blood within the first container.

In another embodiment of the present invention, there is provided a centrifugal separating assembly for separating a fluid biological product into discrete components, the assembly comprising:

a unitary container body defining a first cavity in fluid communication with a second cavity via a common inlet-outlet port, the unitary container body including:

a concave shaped bottom wall extending downwardly from the first tubular sidewall, the concave shaped bottom wall defining an interior surface of the second cavity, a first tubular sidewall extending downwardly from an upper rim of the unitary container body, the first tubular sidewall defining an exterior surface of the unitary container body and the upper rim circumscribing an opening of the unitary container body, and a second tubular sidewall extending downwardly from the upper rim and terminating at the common inlet-outlet port, the second tubular sidewall defining an interior surface of the first cavity; and a cap adapted to fittingly engage the upper rim to form a seal therewith and cover the opening of the unitary container body.

In accordance with a feature of the present invention, the assembly further includes an entry port formed in the cap, the entry port adapted to introduce the fluid biological product into the first cavity; and an exit port formed in the cap, the first exit port adapted to allow removal of discrete components from the first cavity.

In accordance with a further feature of the present invention, the assembly includes an exit port formed in the concave shaped bottom wall, the exit port adapted to allow removal of discrete components from the second cavity.

In accordance with a further feature of the present invention, the unitary container body includes polycarbonate.

In accordance with a further feature of the present invention, the second tubular sidewall is conical shaped.

In accordance with a further feature of the present invention, the first tubular sidewall is concentric with the second tubular sidewall and the second tubular sidewall has a smaller diameter than a diameter of the first tubular sidewall.

In accordance with a further feature of the present invention, the assembly further includes a convex shaped intermediate wall extending inwardly from a peripheral bottom edge of the first tubular sidewall, the convex shaped intermediate wall forming an arched roof of the second cavity, and wherein the common inlet-outlet port is integral with a bottom end of the second tubular sidewall and a central portion of the convex shaped intermediate wall.

In accordance with a further feature of the present invention, the common port is disposed within an interior of the unitary container body and between the first cavity and the second cavity. In accordance with a further feature of the present invention, yet another embodiment of the present invention includes a method of separating a fluid biological product into discrete layers by centrifugation, where the method includes providing a centrifugal separating assembly including a container body defining a first cavity in fluid communication with a second cavity via a common port; introducing the fluid biological product into an entry port of the first cavity; and after introducing the fluid biological product, centrifuging the fluid biological product for a predetermined amount of time to separate the fluid biological product into discrete layers such that a first discrete layer and a second discrete layer formed beneath the first discrete layer remains in the first cavity and a third discrete layer is formed in the second cavity.

In accordance with a further feature of the present invention, the method further includes after centrifuging the fluid biological product, removing the first discrete layer from the first cavity via an exit port; and after removing the first discrete layer from the first cavity, removing the second discrete layer from the first cavity via the exit port.

In accordance with a further feature of the present invention, the method further includes adjusting component ratios of the second discrete layer by, after centrifuging, removing an amount of the third discrete layer from the second cavity via a second exit port and, after removing the amount of the third discrete layer, centrifuging the fluid biological product again.

In accordance with a further feature of the present invention, the first, second, and third discrete layers are a plasma layer, a buffy coat layer, and a red blood cell layer, respectively.

In accordance with another feature of the present invention, a centrifugal separating assembly includes a first container body at least partially defining a first cavity in fluid communication with a second cavity via a common inlet-outlet port; and a second container body receiving at least a portion of the first container body therein such that the second container body forms at least one wall of the second cavity, the first container body disposed to selectively translate relative to the second container body such that the wall of the second cavity is selectively translated so as to selectively adjust a volume of the second cavity.

In accordance with another feature, an embodiment of the present invention further includes a plurality of measurement markings externally visible from an outside environment, each of the plurality of measurement markings disposed to indicate to a user one of a plurality of translation movements of the first container body relative to the second container body that corresponds to a selected predetermined position of a discrete layer of a fluid biological product within the first cavity.

In accordance with yet a further feature of the present invention, the selected predetermined position is a result of a centrifugation of the centrifugal separating assembly after the first container body is moved relative to the second container body according to one of the plurality of translation movements identified by a corresponding one of the plurality of measurement markings.

In accordance with another feature of the present invention, the discrete layer is a buffy coat layer and the selected predetermined position is an optimum position of the buffy coat layer relative to a plasma layer and a red blood cell layer.

In accordance with another feature, an embodiment of the present invention further includes a threading portion on an external surface of the second container body adapted to permit the selective translation of the first container body relative to the second container body.

In accordance with yet another feature, an embodiment of the present invention includes a mating threading portion associated with the first container body and adapted to mate with the threading portion on the second container body in order to selectively translate the first container body relative to the second container body.

In accordance with yet another feature of the present invention, a movement of a cap portion of the first container body selectively translates the first container body relative to the second container body to adjust the volume of the second cavity.

In accordance with another feature, an embodiment of the present invention further includes a cap portion disposed to cover an opening of the first container body into the first cavity; and an entry port defined by the cap portion, the entry port adapted to introduce a fluid biological product into the first cavity.

In accordance with a further feature, an embodiment of the present invention includes a first translation portion on an external surface of the second container body; and a second translation portion on one of the cap portion and the first container body, the second translation portion disposed to matingly engage the first translation portion so as to selectively translate the first container body relative to the second container body to selectively adjust the volume of the second cavity.

In accordance with another feature of the present invention, the first cavity includes a main cavity portion and a neck portion disposed between the main cavity portion and the second cavity, the neck portion having a maximum diameter that is less than a maximum diameter of the main cavity portion and a maximum diameter of the second cavity.

In accordance with yet another feature of the present invention, the first container body is concentric with the second container body.

In accordance with another feature, an embodiment of the present invention provides for a method of separating a fluid biological product into discrete layers by centrifugation, the method including providing a centrifugal separating assembly with a first container body at least partially defining a first cavity in fluid communication with a second cavity via a common inlet-outlet port; and a second container body receiving at least a portion of the first container body therein such that the second container body forms at least one wall of the second cavity, the first container body disposed to selectively translate relative to the second container body such that the at least one wall of the second cavity is selectively translated so as to selectively adjust a volume of the second cavity; introducing the fluid biological product into the first cavity; and after introducing the fluid biological product, centrifuging the fluid biological product to separate the fluid biological product into discrete layers.

In accordance with another feature, an embodiment of the present invention further includes identifying a first position of a buffy coat layer, the buffy coat layer being one of the discrete layers of the fluid biological product.

In accordance with yet another feature, an embodiment of the present invention further includes after identifying the first position of the buffy coat layer, selectively translating the first container body relative to the second container body to selectively adjust a volume of the second cavity.

In accordance with a further feature of the present invention, selectively translating the first container body relative to the second container body includes rotating a cap portion of the first container body.

In accordance with an additional feature, an embodiment of the present invention further includes after selectively translating the first container body relative to the second container body, centrifuging the fluid biological product to re-position the buffy coat layer to a second position different than the first position of the buffy coat layer.

In accordance with yet an additional feature of the present invention, the second position of the buffy coat layer is based on the selectively adjusted volume of the second cavity.

In accordance with yet another feature of the present invention, the discrete layers includes a plasma layer, a buffy coat layer, and a red blood cell layer.

In accordance with yet another feature, an embodiment of the present invention further includes before introducing the fluid biological product, inserting the first container body within the second container body such that a cap portion of the first container body also covers an opening of the second container body.

In accordance with yet another feature, an embodiment of the present invention further includes before introducing the fluid biological product, inserting the first container body within the second container body such that the first container body is concentric with second container body.

Although the invention is illustrated and described herein as embodied in a centrifugal separating assembly, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
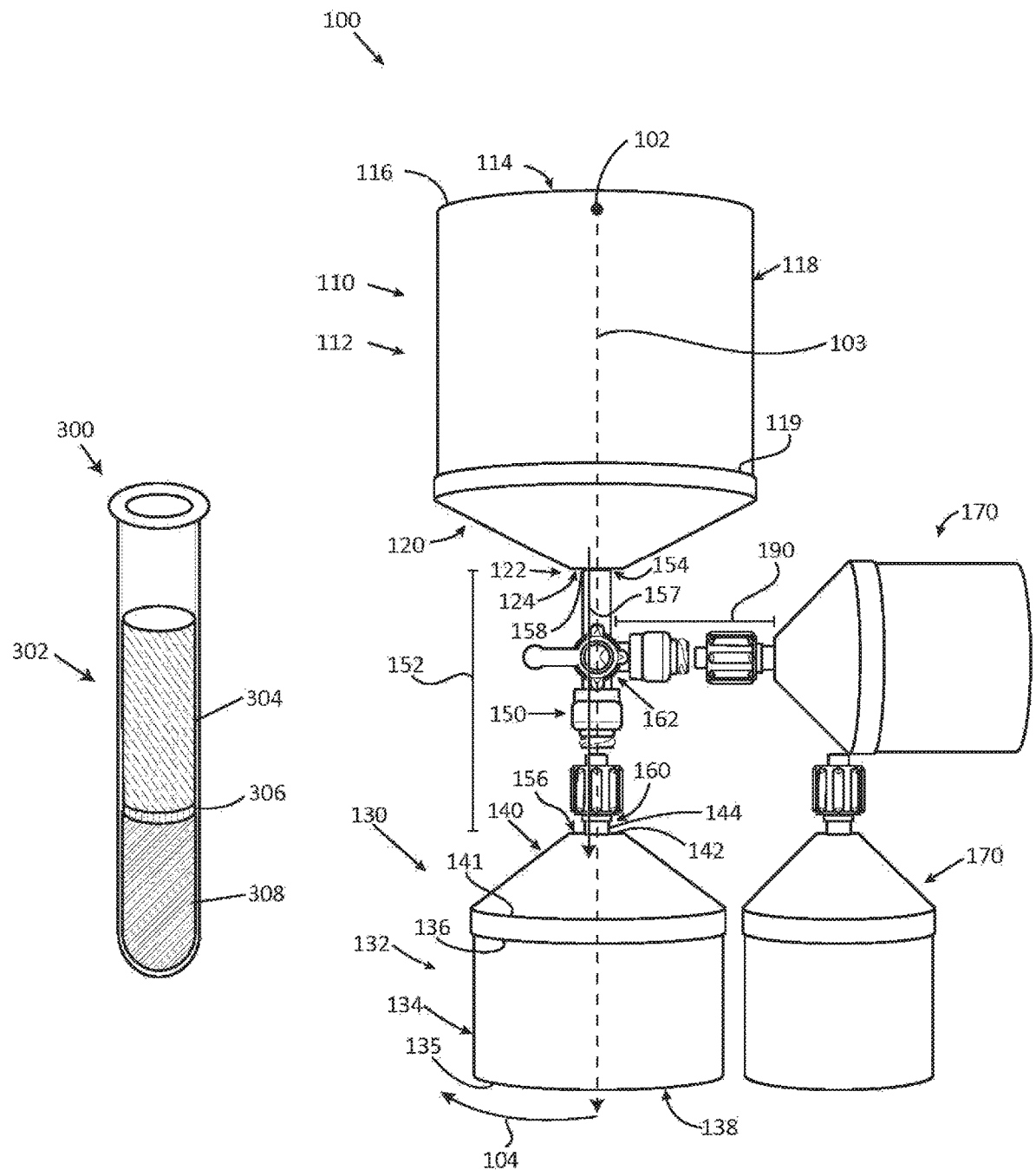
FIG. 1 is an elevation view of a first exemplary embodiment of a centrifuge separating assembly of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient method and device for separating particulates from a solution. Embodiments of the invention provide a centrifugal separating assembly including a first container and a second container coupled via a tubular conduit, the assembly adapted to separate particulates of different densities (or weights) into discrete layers by centrifugation. In addition, embodiments of the invention provide an integral unitary container having a first cavity and a second cavity coupled via a common port and including a multitude of entry and exit ports formed on an external surface of the integral unitary container.

Referring now to FIG. 1, one embodiment of the present invention is shown in an elevation view. FIG. 1 shows several advantageous features of the present invention, but, as will be described below, the invention can be provided in several shapes, sizes, combinations of features and components, and varying numbers and functions of the components. The first example of a centrifugal separating assembly 100, as shown in FIG. 1, includes a first container 110, a second container 130, and a tubular conduit 150 providing fluid communication between the first container 110 and the second container 130, the assembly 100 adapted to channel fluid and particles into a direction during centrifugation to separate particles into discrete layers according to weight and density.

The first container 110 is configured as a storage vessel defining a volumetric space therein capable of holding a defined volume of fluid. The first container 110 includes a circular upper wall 114, a first cylindrical sidewall 118, and a concave shaped bottom wall 120, which, in combination, define a first cavity 112. The first cavity 112 is adapted to receive and store fluid biological product 302, such as blood. The circular upper wall 114 provides a planar surface that covers an upper end of the container 110 to seal fluid therein. The circular upper wall 114 preferably includes an entry port (not illustrated) for injecting fluid into the first cavity 112. The entry port is preferably a needleless self-sealing injection port. The first cylindrical sidewall 118 extends downwardly from a circumferential edge 116 of the circular upper wall 114. The first cylindrical sidewall 118 is bounded between the circular upper wall 114 and the concave shaped bottom wall 120. The concave shaped bottom wall 120 extends inwardly and downwardly from a lower circumferential edge 119 of the first cylindrical sidewall 118. The concave shaped bottom wall 120 terminates at a distal end 122 of the first container 110, the distal end 122 of the first container 110 defining a first tubular conduit receiving aperture 124. The first tubular conduit receiving aperture 124 is configured as a female attachment member and is adapted to mate with a distal end of the tubular conduit 140 for channeling fluid particles to the second container 140 during centrifugation.

The second container 130 is configured as a storage vessel defining a volumetric space therein capable of holding a defined volume of fluid. The second container 130 includes a convex shaped upper wall 140, a second cylindrical sidewall 134, and a circular bottom wall 138, which, in combination, define a second cavity 132 of the inventive assembly 100. The second cavity 132 is adapted to receive and store a predetermined volume of a separated, discrete layer of heavier fluid particles, such as the red blood cell layer 308, after centrifugation. The convex shaped upper wall 140 extends upwardly and inwardly from an upper circumferential edge 136 of the second cylindrical wall 134 and terminates at a distal end 142 of the second container 130, the distal end 142 of the second container 130 defining a second tubular conduit receiving aperture 144. The second tubular conduit receiving aperture 144 is configured as a female attachment member and is adapted to mate with a second, opposing distal end of the tubular conduit 150 for channeling fluid particles into the second container 130. The second cylindrical sidewall 134 extends downwardly from a circumferential edge 141 of the convex shaped upper wall 140. The second cylindrical sidewall 134 is bounded between the convex shaped upper wall 140 and the circular bottom wall 138. The circular bottom wall 138 extends inwardly from a lower circumferential edge 135 of the second cylindrical sidewall 134. The circular bottom wall 138 provides a planar support surface for containing and supporting the separated, discrete layer of heavier fluid particles.

As shown in FIG. 1, the second container 130 can be shaped similar to the first container 110, except that the volumetric storage space provided by the second container 130 can be different than the volumetric space provided by the first container 110. The orientation of the first and second container 110, 130 with respect to the tubular conduit 150 is opposite, as seen in FIG. 1. The first and second containers 110, 130 are preferably made of a polycarbonate material. The inventor of the present invention has discovered that particles do not tend to stick to container walls made of polycarbonate, thus, residue build-up on the interior surface of the containers 110, 130 is reduced and, advantageously, the concentrate of the discrete layers is optimized. In other embodiments, the containers 110 and 130 can include another transparent material, such as glass, or other polymer materials, such as polyethylene, polypropylene, silicone, plastic, and the like.

The walls 114, 118, and 120 of the first container 110 and the walls 140, 134, and 138 of the second container 130 can be integrated such that the first container 110 is formed as a unitary body and the second container 130 is formed as a unitary body. Alternatively, the walls 114, 118, and 120 and the walls 140, 134, and 138 can be fabricated as separate components that are subsequently, removeably attached together. As an example, the circular upper wall 114 and the first cylindrical sidewall 118 can be formed as an integral component, forming a cup member, with the concave shaped bottom wall 120, removeably attached thereto. Although the walls of the containers described herein above 114, 118, 120 and 140, 134, 138 are described as having a particular shape and configuration, it is understood that the description is exemplary and that the container walls described above can be in other shapes and configurations, as well, provided they allow fluid particles to be separated during centrifugation in accordance with the present invention. For example, the bottom wall 120 can be provided resembling a conical shape.

Advantageously, the present invention selects the volume of the containers 110, 130 based on anticipated percentage or ratios of ingredients of the fluid 302. As an example, approximately 40% of human blood is red blood cells 308. Therefore, the second container 130 of the inventive assembly 100 in FIG. 1 is adapted to hold a volume that is approximately 40% of the volume of the first container 110. As the assembly 100 is spun in a centrifugal manner, the heavier red blood cells 308 will force their way toward the distal end 122 of the first container 110, through the tubular conduit 150, and into the bottom of the second container 130 until the second container 130 is entirely or substantially full of red blood cells 308. The second container 130 can then be removed and its contents, i.e. red blood cells 308 in this example, can be utilized, as desired.

The tubular conduit 150 extends, linearly, a length 152 between a first distal end 154 and a second distal end 156 of the tubular conduit 150. The first and second distal ends 154 and 156 are engaged with the first and second tubular conduit receiving apertures 124 and 144, respectively, defining a fluid passageway 157 between the first and second container 110 and 130, which fluid passageway 157 is fluid impermeable and provides fluid communication between the first and second containers 110 and 130. When the first distal end 154 is engaged with the first tubular conduit receiving aperture 124, a first fluid-impermeable seal 158 is formed. Likewise, when the second distal end 156 is engaged with the second tubular conduit receiving aperture 144, a second fluid-impermeable seal 160 is formed. The tubular conduit 150 can be any length and diameter, but is preferably a length and diameter that optimizes fluid flow. A valve 162 can be provided at a point along the length 152 of the tubular conduit 150. In another embodiment, the valve 162 can preferably be replaced with a self-sealing port.

In an alternative embodiment, a third container 170 is provided. The third container 170 can be substantially the same as the second container 130, thus a description of the structure of the third container 170 is not provided, for brevity. The only substantial difference between the third container 170 and the second container 130 is the third container 170 is preferably sized to contain a volume equal to the anticipated percentage of a middle layer 306 anticipated to result from centrifugation. The third container 170 can be adapted to engage a second linear length 190 of the tubular conduit 150, with the second linear length 190 being substantially perpendicular to the first length 152 of the tubular conduit 150, as illustrated in FIG. 1.

When in use, a user places the centrifugal separating assembly 100 in a centrifuge. The assembly 100 is rotated in a centrifugal movement where the first container 110 is closest to an imaginary axis of rotation 102 and the second container 130 is distally located along an imaginary pendulum swing arm 103 with reference to the first container 110.

In other words, during a centrifugal movement, the second container 130 will travel a further distance than will the first container 110. This rotation movement is represented by line 104 in FIG. 1. Heavier components of the fluid product 302 within the first container 110 will be pulled by a centrifugal force, through the tubular conduit 150, and into the second container 130. The molecularly heavier weighing ingredients will naturally be pulled closer to the bottom of the second container 130, i.e. further away from the first container 110 than the other less-heavy discrete components. Therefore, the first and second containers 110, 130 will have a separation of discrete components similar to what is shown in the test tube 300 in FIG. 1.

More specifically, if the fluid product 302 was human blood, after one centrifugation spin cycle, a majority of the heavier red blood cells 308 would be forced into the second container 130. The second container 130 is preferably sized to hold the anticipated percentage of red blood cells 308 (e.g. 40%). At the same time, the lighter plasma layer 304 and the buffy coat layer 306 are separated, but remain in the first container 110. Subsequently, the second container 130 can be swapped out for the third container 170 at the second distal end 156 of the tubular conduit 150. Next, the user initiates another centrifugation spin cycle. After the second centrifugation spin cycle, the buffy coat layer 306 is forced into the third container 170. The third container 170 is preferably sized to hold the anticipated percentage of the buffy coat layer 306 (e.g. 10%). Thus, after two spin cycles, each layer is separated and contained within a distinct container, ready for a desired use.

In the alternative embodiment, the third container 170 is already attached at the second linear length 190 of the tubular conduit 150, eliminating the additional step of swapping out the second and third containers 130, 170. Accordingly, during the second centrifugation spin cycle, the second container 130 is filled to capacity; therefore, the excess buffy coat layer 306 will naturally be forced into the third container 170.

Figure 2:
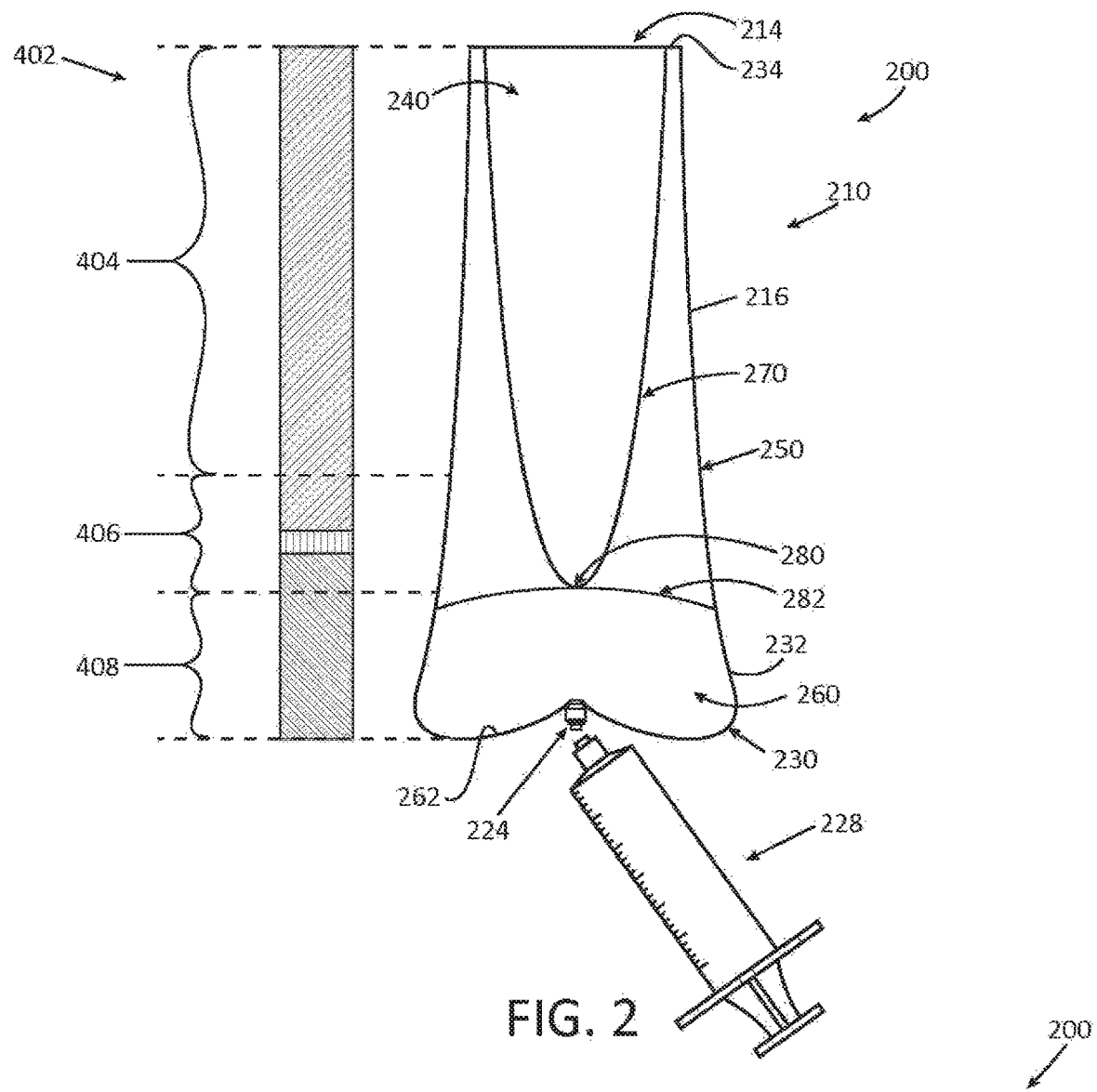
FIG. 2 is a schematic side elevation view of a second exemplary embodiment of a centrifuge separating assembly of the present invention.
Figure 3:
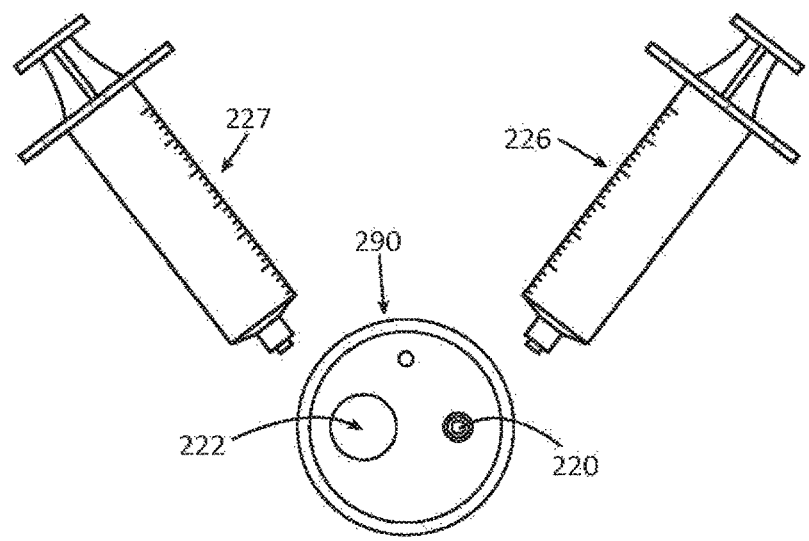
FIG. 3 is a top plan view of a cap of the centrifuge separating assembly originally introduced in FIG. 2.
Figure 4:
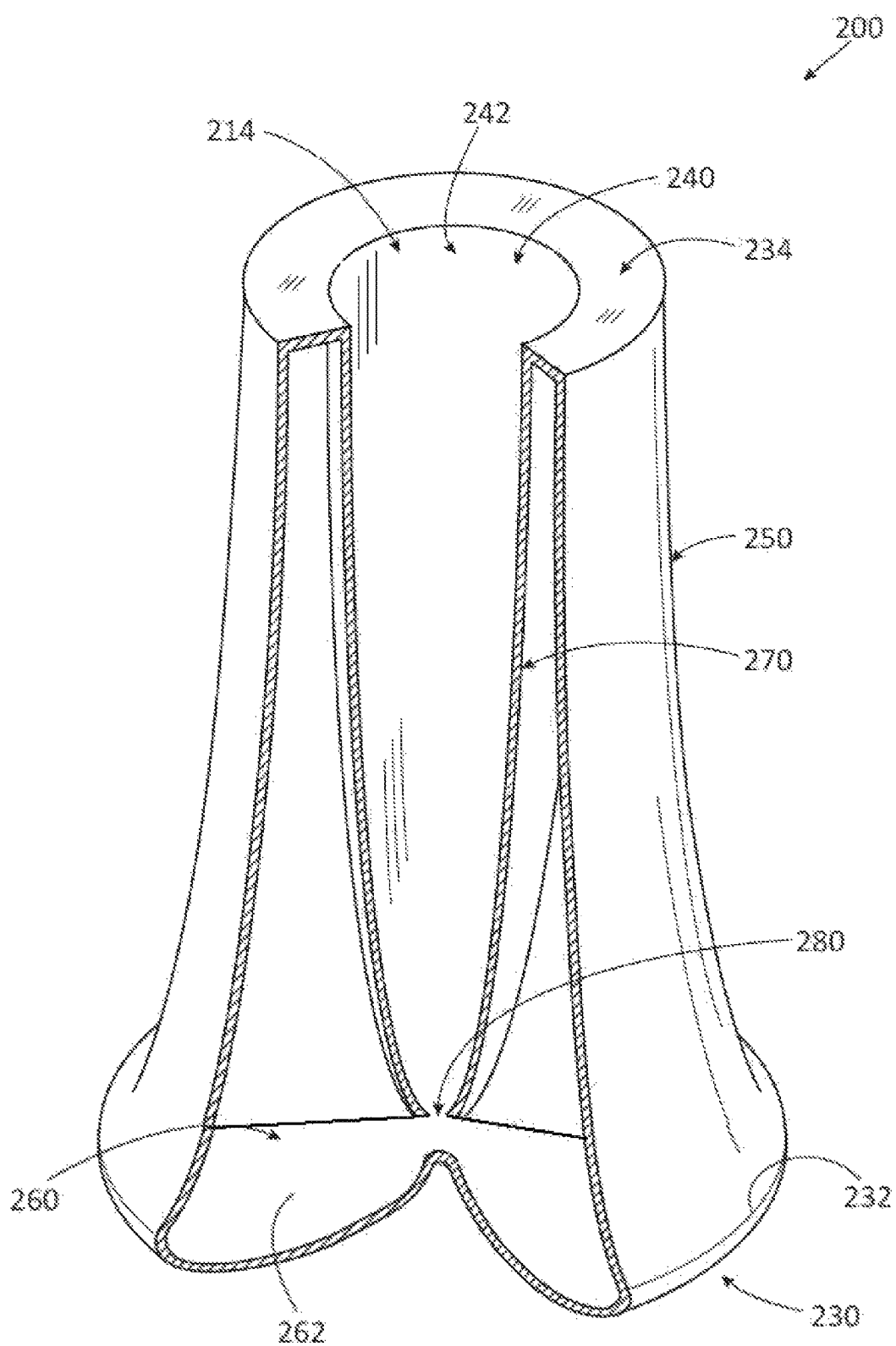
FIG. 4 is a perspective view of the centrifuge separating assembly originally introduced in FIG. 2.

Referring now to FIGS. 2-4, yet another alternative embodiment is illustrated. Another exemplary centrifugal separating assembly 200, as shown in FIGS. 2-4, includes a unitary container body 210, in which a first and a second container are integral, and a cap 290 adapted to seal the container body 210.

The unitary container body 210 defines a first cavity 240 in fluid communication with a second cavity 260 via a common inlet-outlet port 280. The unitary container body 210 may be manufactured using any of the well-known manufacturing processes known by those skilled in the art, including injection molding, vacuum forming, machining, and the like. The unitary container body 210 includes a concave shaped bottom wall 230, a convex shaped intermediate wall 282, a first tubular sidewall 250, and a second tubular sidewall 270.

The first tubular sidewall 250 extends downwardly from an upper rim 234 of the unitary container body 210, the first tubular sidewall 250 defining an exterior surface 216 of the unitary container body 210. The upper rim 234 circumscribes an opening 214 of the unitary container body 210. The first tubular sidewall 250 transitions into the concave shaped bottom wall 230.

The concave shaped bottom wall 230 defines an interior support surface 262 of the second cavity 260 and defining a receiving section for receiving and storing a separated, discrete component layer. The concave shaped bottom wall 230 curves inward toward a center of the unitary container body 210 along a bottom peripheral edge 232 of the first tubular sidewall 250. A first exit port 224 is formed in the concave shaped bottom wall 230, preferably at the center where the bottom wall 230 curves inwards. The first exit port 224 is adapted to allow removal of discrete components from the second cavity 260, preferably with a needleless syringe 228.

The convex shaped intermediate wall 282 provides a curved surface within the interior of the unitary container body 210 that increases movement of lighter particles, or cells to rise into the first cavity 240. The convex shaped intermediate wall 282 extends inwardly from a peripheral bottom edge of the first tubular sidewall 250, forming an arched roof of the second cavity 260. The convex shaped intermediate wall 282, the concave shaped bottom wall 230, and a segment of the first tubular sidewall 250 disposed therebetween, defines the second cavity 260.

The second tubular sidewall 270 extends downwardly from the upper rim 234 and terminates at the common inlet-outlet port 280, the second tubular sidewall 270 defining an interior surface 242 of the first cavity 240. The second tubular sidewall 270 is preferably conical shaped and is preferably concentric with the first tubular sidewall 250, with the second tubular sidewall 270 having a smaller diameter than a diameter of the first tubular sidewall 250.

The common inlet-outlet port 280 is preferably formed integrally with a bottom end of the second tubular sidewall 270 and a central portion of the convex shaped intermediate wall 282. The common port 280 is disposed within the interior of the unitary container body 210, between the first and second cavities 240 and 260. The common port 280 can be a self-sealing port. As with the centrifugal separating assembly 100, the walls 230, 250, and 270 of the centrifugal separating assembly 200 are preferably made of polycarbonate to reduce residue build-up on the walls.

The cap 290 is adapted to fittingly engage the upper rim 234 of the unitary container body 210, forming a seal therewith and covering the opening 214. The cap 290 can be configured to selectively, releasably engage the upper rim 234, or the cap 290 can be formed integrally with the upper rim 234 of the unitary container body 210. The cap 290 can have a generally planar surface. An entry port 220 is formed in the cap 290, the entry port 220 adapted to introduce the fluid biological product 402 into the first cavity 240. The entry port 220 is preferably a needleless self-sealing injection port, configured to allow injection of fluids with a needleless syringe 226. A second exit port 222 can also be formed in the cap 290, the second exit port 222 adapted to allow discrete components from the first cavity 240 to be removed, preferably with a needleless syringe 227.

Figure 5:
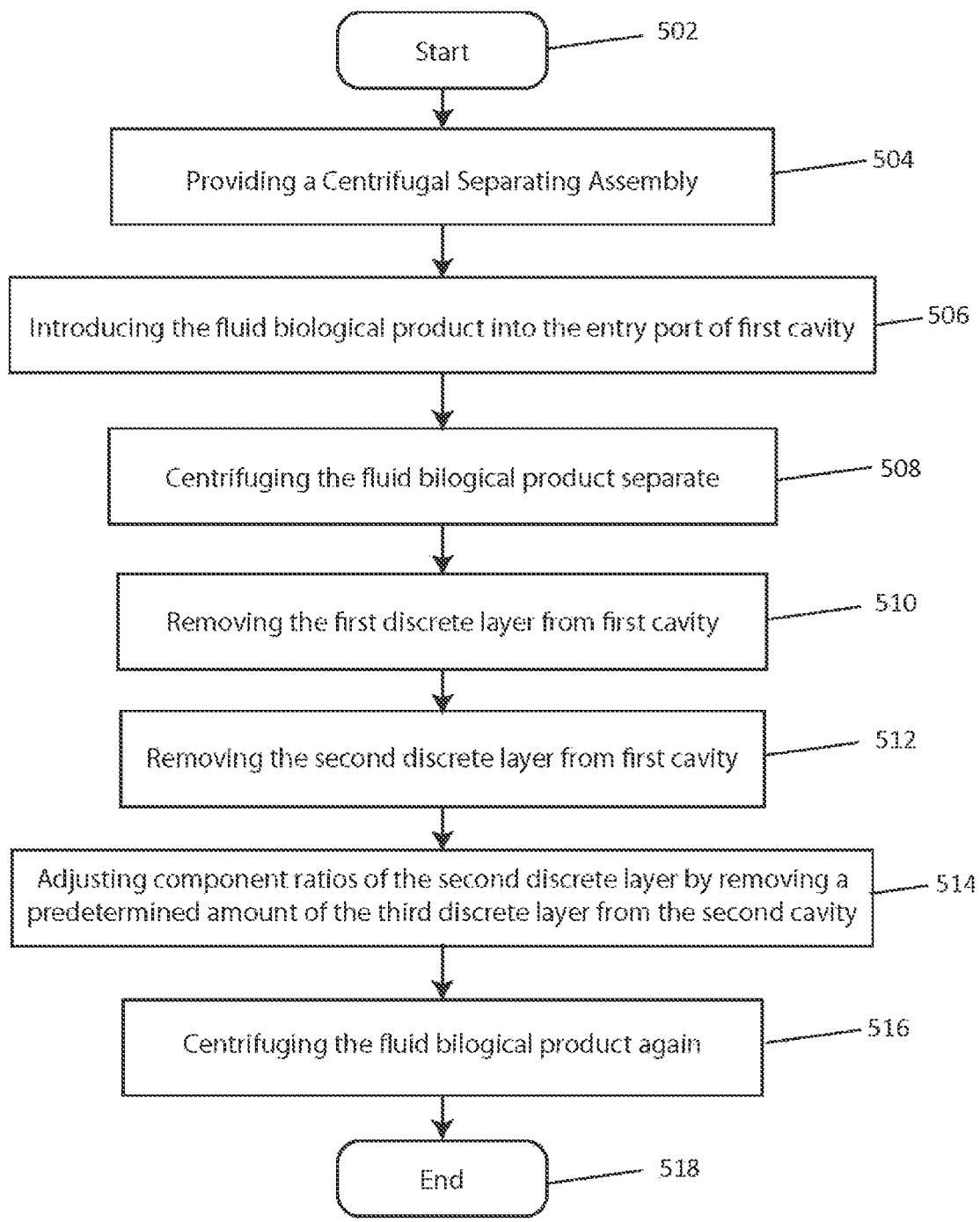
FIG. 5 is a flow diagram illustrating a process for using the centrifuge separating assembly originally introduced in FIG. 2.

Referring now primarily to FIGS. 5 and 2, the present invention provides a process for separating the fluid biological product 402 into first, second, and third discrete layers 404, 406, and 408. For illustrative purposes, the fluid biological product 402 is human blood and the discrete layers are a plasma layer 404, a buffy coat layer 406, and a red blood cell layer 408. The process begins at step 502 and continues immediately to step 504, where a user provides a centrifugal separating assembly, such as the centrifugal separating assembly 200 having a unitary container body 210 defining a first cavity 240 in fluid communication with a second cavity 260 via a common inlet-outlet port 280. In step 506, the user introduces the fluid biological product 402 into the entry port 220 of the first cavity 240. The user can use a needleless syringe 226 to inject human blood 402 into the entry port 220. After introducing the human blood 402, in step 508, the user can centrifuge the blood 402 for a predetermined amount of time and at a specific speed (g-force) to separate the blood 402 into discrete layers such that a first discrete layer 404 and a second discrete layer 406, formed immediately beneath the first discrete layer 404, remains in the first cavity 240 and a third discrete layer 408 is formed in the second cavity 260. The centrifuging forces separation of the components according to weight and forces the third discrete layer 408 to travel from the first cavity 240 into the second cavity 260. In step 510, after centrifuging the blood 402, the user removes the first discrete layer 404 from the first cavity 240 via the second exit port 222. The user can remove the first discrete layer 404 by extracting it with the syringe 227, which in one embodiment can be a depth-gauged syringe. Measurement markings can be provided on the surface of the second tubular sidewall 270 to guide the user as to the amount of fluid particles withdrawn from the first cavity 240. In step 512, after removing the first discrete layer 404 from the first cavity 240, the user removes the second discrete layer 406 from the first cavity 240. In many applications, the second, middle layer is the desired layer. Regarding human blood samples, the buffy coat 406 is desired for various advantageous applications.

In step 514, the user can adjust component ratios of the buffy coat 406 in the bottom of the first cavity 240 by, after centrifuging the blood sample 402 in step 508, removing a predetermined amount of the red blood cells 408 from the second cavity 260 and then, in step 516, the user can centrifuge the blood sample 402 again. This will force more red blood cells 408 into the second cavity 260, advantageously reducing the percentage of red blood cells 408 within the buffy coat 406 in the bottom of the first cavity 240. The user can repeat steps 514 and 516 until the desired component ratios of the buffy coat 406 are achieved. The process ends at step 518. Although the exemplary method discusses centrifugation of human blood, it is understood that that the fluid biological product can be other fluids, such as, for example, non-human blood, or bone marrow.

Referring now primarily to FIGS. 6-18, yet another exemplary embodiment of a centrifugal separating assembly 600 for separating a fluid biological product into discrete layers and a corresponding method of using the assembly 600 to adjust a position of a discrete layer of fluid biological product is described.

In one embodiment, the centrifugal separating assembly 600 includes a first container body 800 and a second container body 802. The container bodies 800 and 802 can be made of a transparent material, such as glass, or other polymer materials, such as polyethylene, polypropylene, silicone, plastic, and the like. The container bodies 800 and 802 may be of a rigid material. In a preferred embodiment, at least a portion of the outer container body, i.e., the second container body 802, is of a transparent material so that markings on the inside of the centrifugal separating assembly 600 are externally visible. Such markings may guide the user in certain methods of using the centrifugal separating assembly 600 to adjust a position of at least one of discrete layers of fluid biological product, as will be described herein below. In a further embodiment, both of the container bodies 800 and 802 may be at least partially made of a transparent material so that the discrete layers can be externally visible.

The first container body 800 may at least partially define a first cavity 804. The fluid biological product may be introduced into the first cavity 804 for centrifugation via an entry port 700. The entry port 700 may be defined by a cap portion 702 of the centrifugal separation assembly 600. The cap portion 702 may be disposed to cover an opening 806 defined by the first container body 800 into the first cavity 804.

Figure 13:
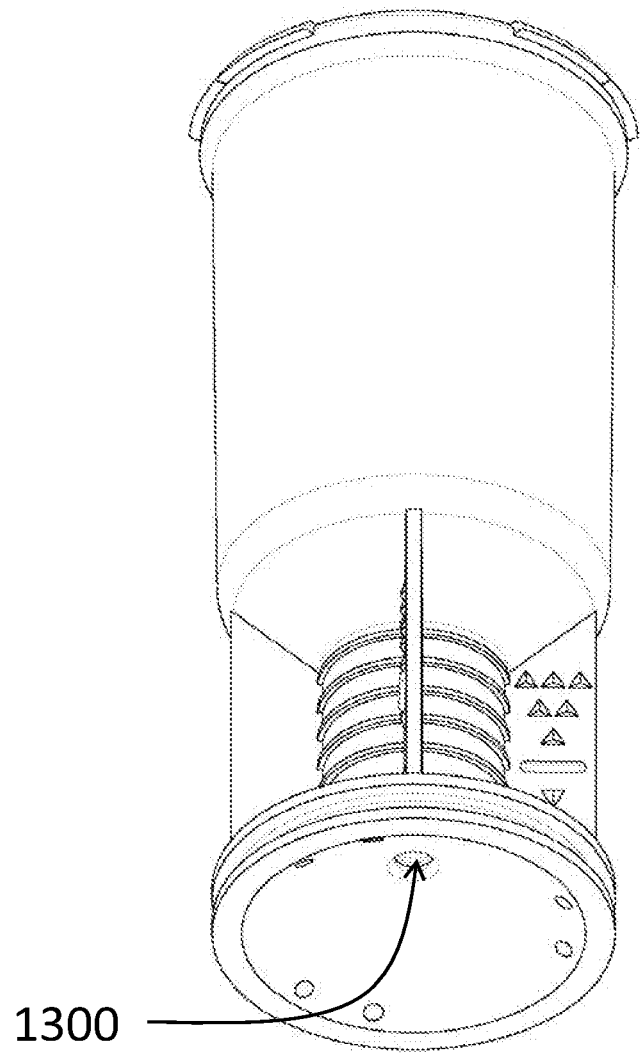
FIG. 13 is a fragmentary, upward-looking perspective view of the centrifugal separating assembly introduced in FIG. 6, illustrating a bottom side of the first container.
Figure 14:
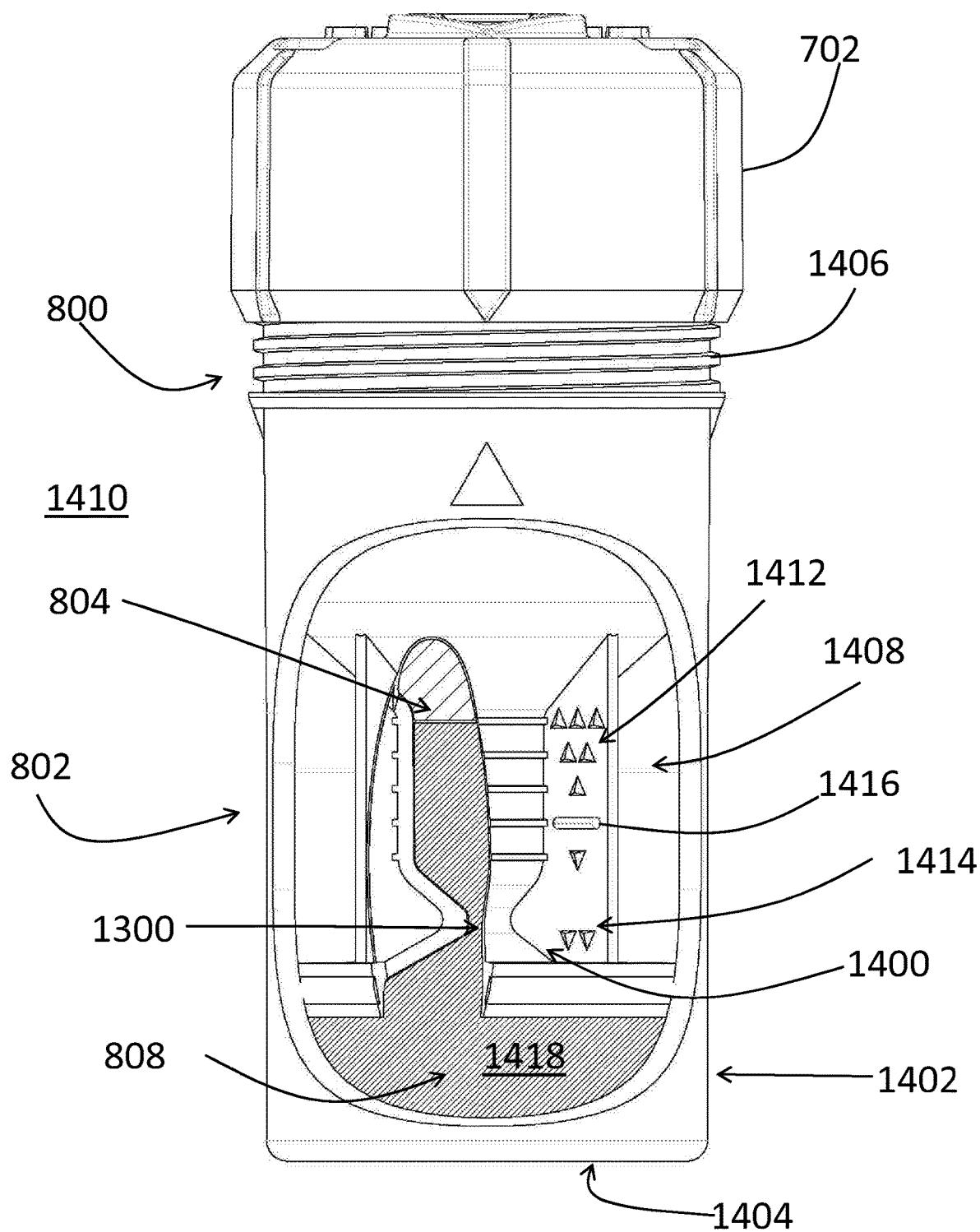
FIGS. 14-17 are partial cross-sectional views of the centrifugal separating assembly introduced in FIG. 6, illustrating three (3) discrete layers resulting from centrifuging blood in the centrifugal separating assembly.
Figure 15:
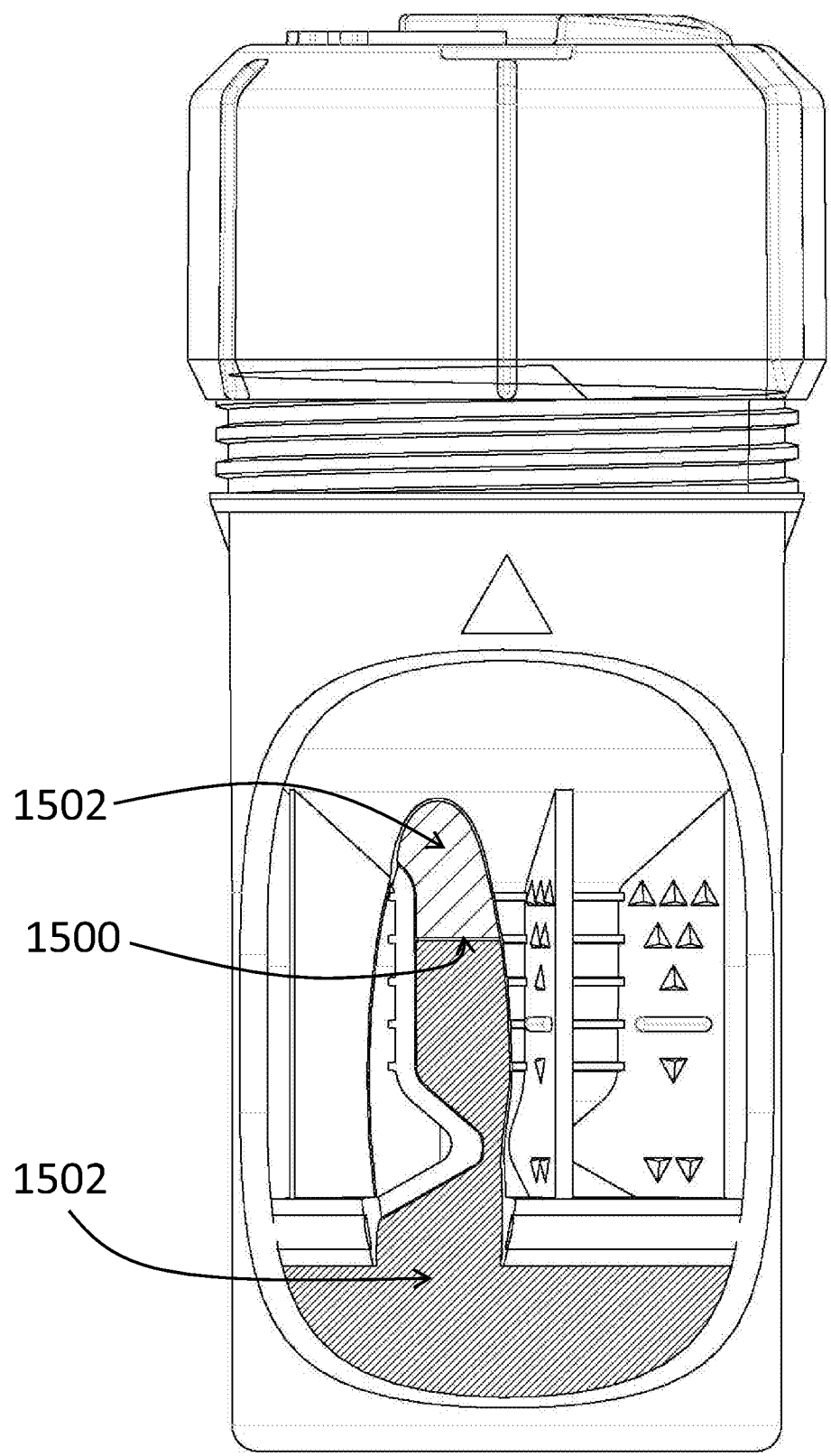

In another embodiment, the second container 802 at least partially defines a second cavity 808. The first cavity 804 may be in fluid communication with the second cavity 808 via a common inlet-outlet port 1300, as can be seen in FIGS. 13-14. The common inlet-outlet port 1300 may be defined by walls of the first container body 800; yet when the first container body 800 is disposed within the second container body 802 the common inlet-outlet port 1300 provides for fluid communication between the first cavity 804 and the second cavity 808.

The shape of the first and second cavities 804 and 808 may be provided in various forms and configurations. With brief reference specifically to FIG. 16, in one embodiment, the first cavity 804 may include a main cavity portion 1600 and a neck portion 1602. The neck portion 1602 may be disposed between the main cavity portion 1600 and the second cavity 808. In a further embodiment, the neck portion 1602 may have a maximum diameter 1604 that is less than a maximum diameter 1608 of the main cavity portion 1600 and less than a maximum diameter 1606 of the second cavity 808. In other words, the neck portion 1602 may be narrower that the other portions of the first and second cavities 804 and 808. Such configuration may be advantageous in certain methods of the present invention, as will be discussed herein in more detail below, with reference to the flow chart of FIG. 18. In a preferred embodiment, each of the maximum diameter 1608 of the main cavity portion 1600 and the maximum diameter 1606 of the second cavity 808 may be in a range of 33-35 millimeters, while the maximum diameter 1604 of the neck portion 1602 may be 14 millimeters. In another embodiment, the ratio of the diameter 1604 of the neck portion 1602 to the diameters 1606, 1608 of the other wider portions 1600, 808 is 2:5. In yet other embodiments, the ratio of diameters 1604, 1606, 1608 may be outside of these ranges, but should still provide for the neck portion 1602 to be substantially narrower than the other wide portions 1600, 808. The neck portion 1602 may be the portion of the first cavity 804 within which the desired position of the discrete layer is located. In other embodiments, the cavities 804 and 808 may be provided in yet other configurations.

In one embodiment, the second container body 802 is configured to receive at least a portion of the first container body 800 therein such that the second container body 802 forms at least one wall 1404 of the second cavity 808. As can be seen in FIG. 14, the second cavity 808 may be partially defined by a lower portion 1400 of the first container body 800 and partially defined by a lower portion 1402 of the second container body 802. In other words, the second container body 802 may be considered to form at least one wall 1404 of the second cavity 808 when the first container body 800 is received within the second container body 802. In a further embodiment, the wall 1404 may be a bottom wall of the second container body 802.

Importantly, translation of the first container body 800 relative to the second container body 802 changes a volume of the second cavity 808, which can be used by methods of embodiments of the present invention to select a desired position of one of the discrete layers of the fluid biological product as a result of centrifugation. Stated another way, the first container body 800 may be disposed to be selectively translated relative to the second container body 802 such that the wall 1404 of the second cavity 808 is selectively translated so as to selectively adjust a volume of the second cavity 808. Stated yet another way, as the first container body 800 is moved up and down, relative to the second container body 802, it should be apparent that the volume of the second cavity 808 is also adjusted.

Figure 8:
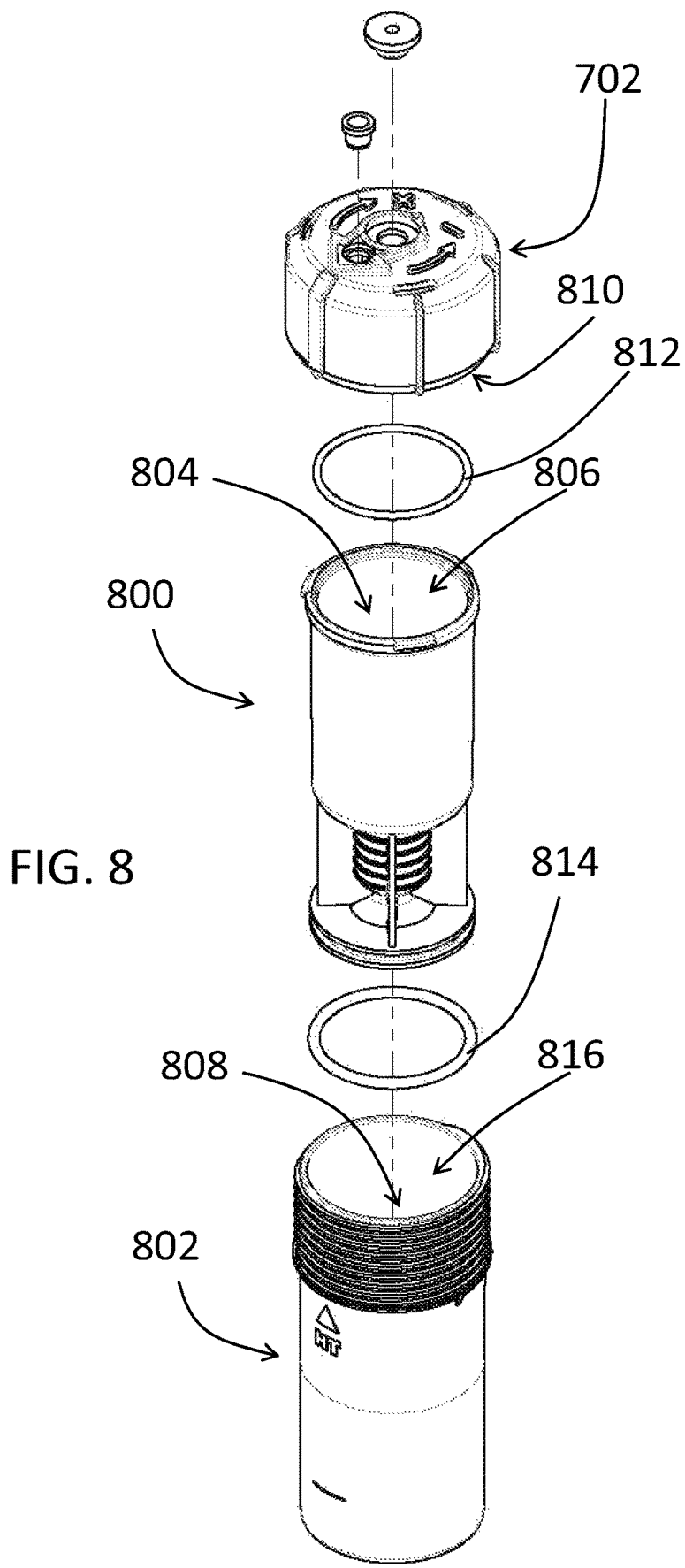
FIG. 8 an exploded view of the centrifugal separating assembly introduced in FIG. 6.
Figure 9:
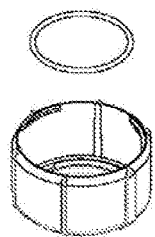
FIG. 9 is a fragmentary, exploded view of the centrifugal separating assembly introduced in FIG. 6, illustrating a portion of a cap.
Figure 10:
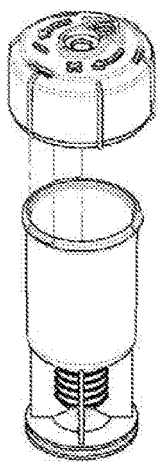
FIG. 10 is a fragmentary, exploded view of the centrifugal separating assembly introduced in FIG. 6, illustrating the cap and a first container.
Figure 11:
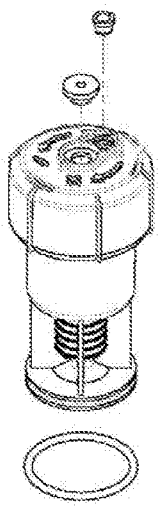
FIG. 11 is a fragmentary view of the centrifugal separating assembly introduced in FIG. 6, illustrating the cap and the first container in a partially assembled configured.
Figure 12:
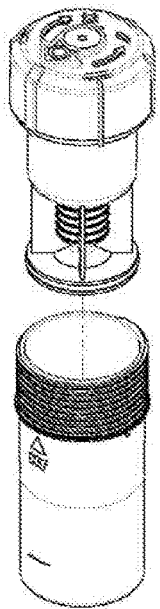
FIG. 12 is a perspective view of the centrifugal separating assembly introduced in FIG. 6, in a non-assembled configuration.

Many different translation mechanisms can be utilized to change the volume of the second cavity 808 in accordance with the present invention. In one embodiment, the cap portion 702 may be coupled to the first container body 800 in a stationary manner, such that a movement of the cap portion 702 selectively translates the first container body 800 relative to the second container body 802 to adjust the volume of the second cavity 808. In a further embodiment, there may be a threading portion 810 associated with the first container body 800 and a mating, threading portion 1406 associated with the second container body 802. The threading portions 810 and 1406 may be configured to mate with one another in a helical configuration such that rotation of the first container body 800 moves the same relative to the second container body 802, thereby permitting selective adjustment of the volume of the second cavity 808. In the depicted embodiment, as can be seen in FIGS. 8 and 14, the threading portion 1406 is on an external surface of the second container body 802 and the mating, threading portion 810 is disposed on an inner surface of the cap portion 702. In another embodiment, the threading portion 810 may be otherwise associated with the first container body 800, such as, for example, by being disposed on an external surface of the first container body 800. Of course, the mating threading portion 1406 associated with the second container body 802 should be disposed to contact the threading portion 810 associated with the first container body 800.

The threading portions 1406 and 810 may be considered first and second translation portions 1406 and 810. In other embodiments, such first and second translation portions 1406 and 810 may be formed as other non-threaded translation mechanisms, such as, for example, a sliding telescoping translation mechanism, a track mechanism, etc. In a preferred embodiment, the centrifugal separating assembly 600 should be configured such that translation of the first container body 800 relative to the second container body 802 may be performed by a user precisely so that such movement can be accurately correlated to a selected, predetermined position of one of the discrete layers of the fluid biological product.

To that end, in one embodiment, the centrifugal separating assembly 600 may include a plurality of measurement markings 1408 that are externally visible from an outside environment 1410. Such measurement markings 1408 may guide the user as to the magnitude and direction in which to move the first container body 800 relative to the second container body 802 in order to obtain a desired position of one of the discrete layers. In one embodiment, each of the plurality of measurement markings 1408 is disposed to indicate to the user one of a plurality of translation movements of the first container body 800 relative to the second container body 802 that corresponds to the selected, predetermined position of the discrete layer of the fluid biological product. The selected position can be considered the position of the discrete layer that is intended to result from a centrifugation of the centrifugal separating assembly 600 after the first container body 800 is moved relative to the second container body 802 according to the selected translation movement that is identified by the indicated measurement marking 1408. An example is described herein below in more detail.

In the depicted embodiment, the plurality of measurement markings 1408 includes a plurality of upwardly-oriented triangles 1412, a plurality of downwardly-oriented triangles 1414, and a straight-line bar indicator 1416. In other embodiments, other shapes, sizes, markings, location of marking, etc. may be used as measurement markings 1408 to guide the user. An example of the use of the measurement markings 1408 to so guide the user, in accordance with embodiments of the present invention, is described herein below.

In a preferred embodiment, the selected predetermined position of the discrete layer may be an optimum position of the layer relative to the other discrete layers. With brief reference to FIG. 15, in one embodiment, the discrete layer is a buffy coat layer 1500 and the selected position is an optimum position of the buffy coat layer 1500 relative to the plasma layer 1502 and the red blood cell layer 1504. The selected position may be considered a predetermined position. Such optimum position of the buffy coat layer 1500 is known by those of ordinary skill in the blood centrifugation arts. As is known in the art, the position of the buffy coat layer 1500, resulting from a centrifugation of a blood sample, relative to the plasma layer 1502 and the red blood cell layer 1504 can vary from patient to patient depending on a number of factors, including a hydration level of the patient when the blood sample is taken. It is desired by embodiments of the present invention, to provide devices and methods of intentionally positioning the buffy coat layer 1500 at a predetermined and/or optimum position relative to the other discrete layers 1502, 1504. A preferred process of doing so is described herein below, with reference to primarily FIGS. 14-17 and the flow chart depicted in FIG. 18.

Figure 18A:
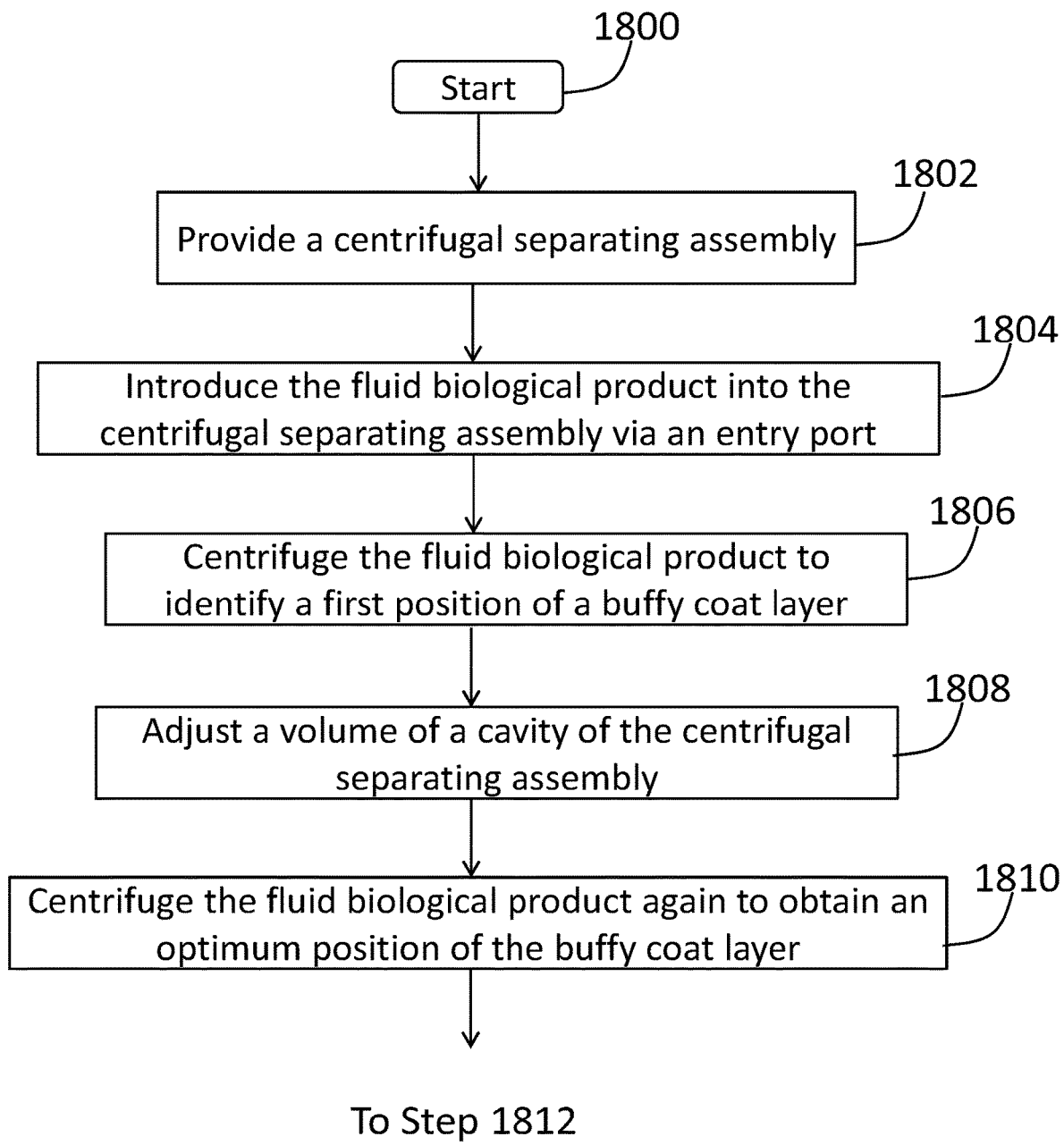
FIGS. 18a-b depict a flow chart of an exemplary method of using the centrifugal separating assembly introduced in FIG. 6 to selectively adjust a position of a buffy coat layer within the assembly and selectively adjust the concentration of certain components within the buffy coat layer.
Figure 18B:
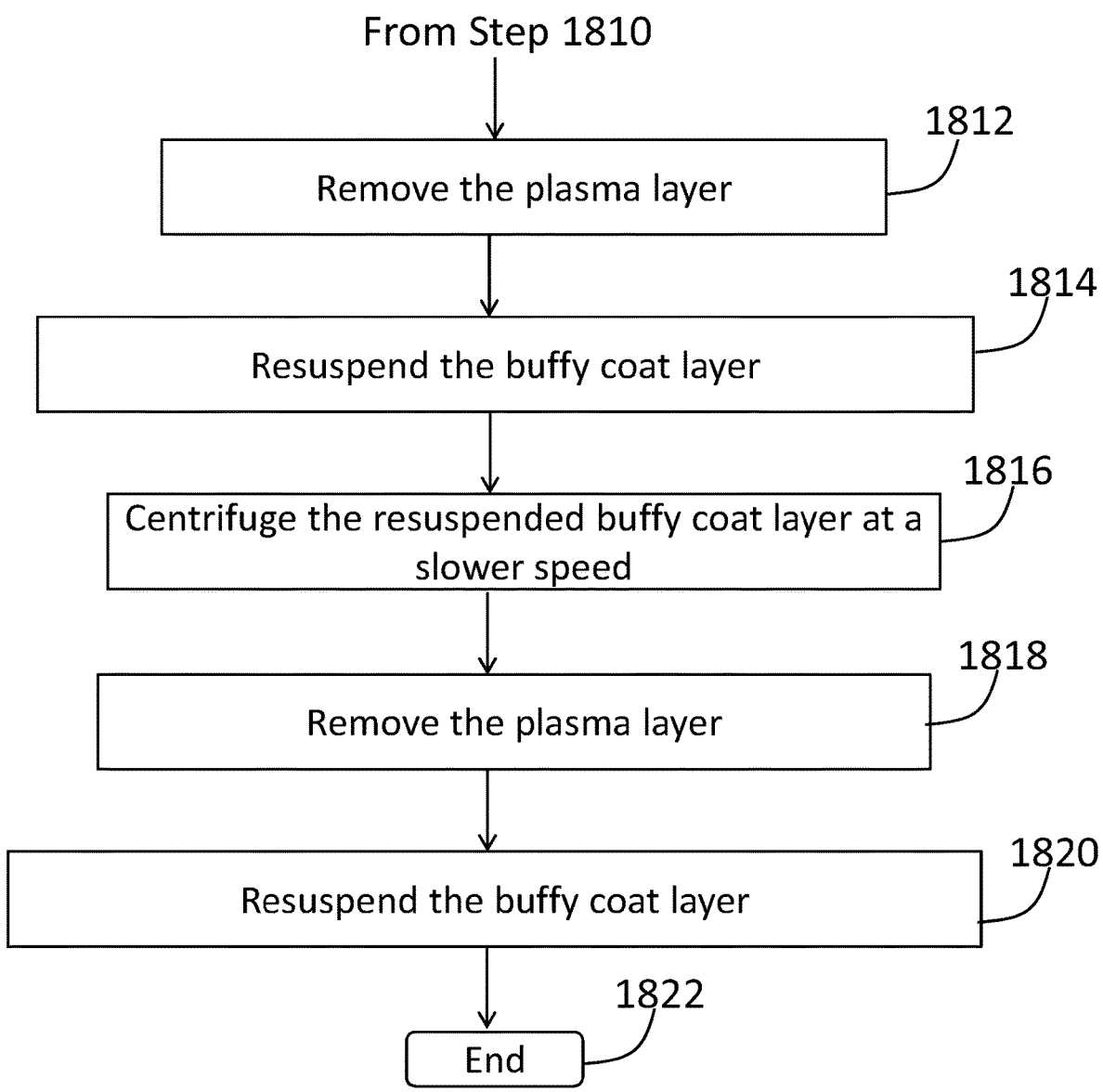

Although FIG. 18 shows a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIG. 18 for the sake of brevity. In some embodiments, some or all of the process steps included in FIG. 18 can be combined into a single process.

The process may begin at step 1800 and may continue immediately to step 1802, where a user provides a centrifugal separating assembly, such as the centrifugal separating assembly 600, described herein above. This step may also include assembling the various components of the centrifugal separating assembly 600, as shown in FIGS. 9-12. One or more O-rings 812, 814 may be used to secure and/or seal the components (such as the first container body 800, the second container body 802, and the cap portion 702) together. Step 1802 may further include at least partially inserting the first container body 800 (coupled to the cap portion 702) within the second container body 802 such that they are concentric with one another. In a further embodiment, such insertion is such that the cap portion 702 of the first container body 800 also covers an opening 816 into the second container body 802.

Figures 6, 7:
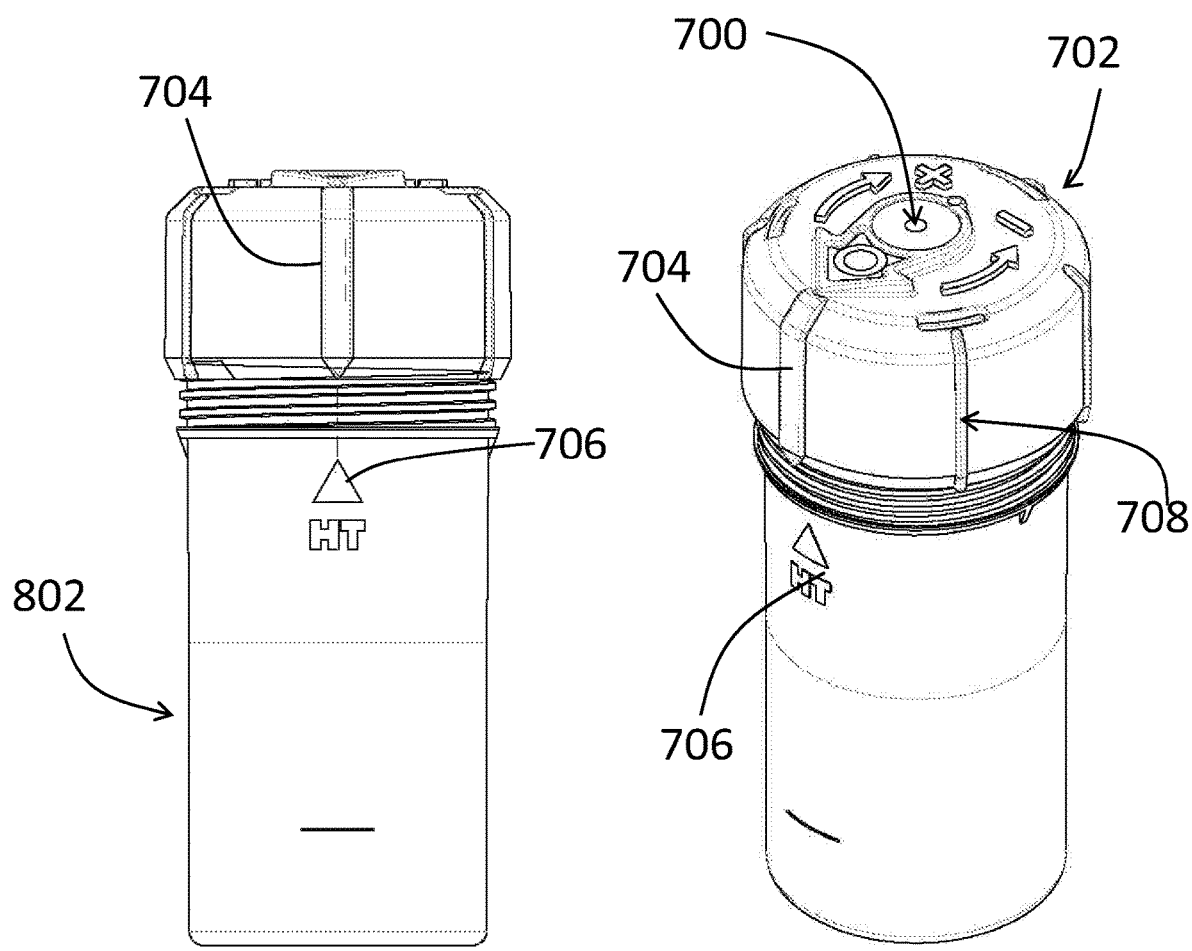
FIG. 6 is front elevational view of a third exemplary embodiment of a centrifugal separating assembly in accordance with the present invention.
FIG. 7 is a perspective view of the centrifugal separating assembly introduced in FIG. 6.

In yet a further embodiment, the cap portion 702 may include a default cap position marking 704 and the second container body 802 may include a default container marking 706, each being externally visible and configured to align with one another (as shown in FIGS. 6-7) at a default position at the outset of the process before any translation movements occur. As should be recognized, in order to accurately measure translation of the first container body 800 relative to the second container body 802, such initial or default position should first be obtained by the user.

In step 1804, the user may introduce a fluid biological product 1418 into the centrifugal separating assembly 600. More specifically, in one embodiment, the user may introduce the fluid biological product 1418 via the entry port 700 of the cap portion 702, such as, for example, by injecting the product 1418 into the entry port 700 with a syringe. After introducing the fluid biological product 1418 into the first cavity 804, the user may centrifuge the product 1418, in step 1806, for an amount of time and at a specific speed (g-force) to separate the fluid biological product 1418 into discrete layers. In a most preferred embodiment, the fluid biological product 1418 is human blood and centrifugation may separate the blood 1418 into three discrete layers, namely, the buffy coat layer 1500, the plasma layer 1502, and the red blood cell layer 1504, as described herein above with reference to FIGS. 1-5.

Step 1806 may also include identifying a first position of the buffy coat layer 1500 that results from a first centrifugation of the fluid biological product 1418. Such identification step of the first, default, position of the buffy coat layer 1500 may inform the user, in conjunction with the measurement markings 1408, as to the required translation movement to obtain the optimum position of the buffy coat layer 1500 (during a subsequent centrifugation of the fluid biological product 1418). For example, FIG. 14 shows the first position of the buffy coat layer 1500 at a position corresponding to a three upwardly oriented triangle measurement marking 1412. Such measurement marking 1412 may indicate to the user the magnitude and direction of rotation required to obtain the desired position of the buffy coat layer 1500.

The cap portion 702 may also include cap markings 708. In the exemplary embodiment, six (6) cap markings 708 are disposed radially, equidistant on the cap portion 710. Each of the cap markings 708 corresponds to a $1/6^{th}$ rotational turn of the cap portion 702. Each triangle marking may represent one (1) $1/6^{th}$ rotational turn of the cap portion 702 such that three triangles indicates three (3) $1/6^{th}$ rotational turns of the cap portion 702; two triangles indicates two (2) $1/6^{th}$ rotational turns of the cap portion 702; and one triangle indicates one (1) $1/6^{th}$ rotational turn of the cap portion 702. Upwardly-oriented triangles 1412 may indicate a first rotation direction, i.e., one of a clockwise or counter-clockwise rotation. Accordingly, the downwardly-oriented triangles 1414 may indicate a rotational direction that is opposite the rotational direction indicated by the upwardly-oriented triangles. In the exemplary embodiment, rotation in a clockwise direction is indicated by the upwardly-oriented triangles 1412 and rotation in a counter-clockwise direction is indicated by the downwardly-oriented triangles 1414; however, it should be understood that other embodiments may be configured in other ways. The desired or optimum position of the buffy coat layer 1500 may be indicated by the straight-line bar indicator 1416.

Figure 17:
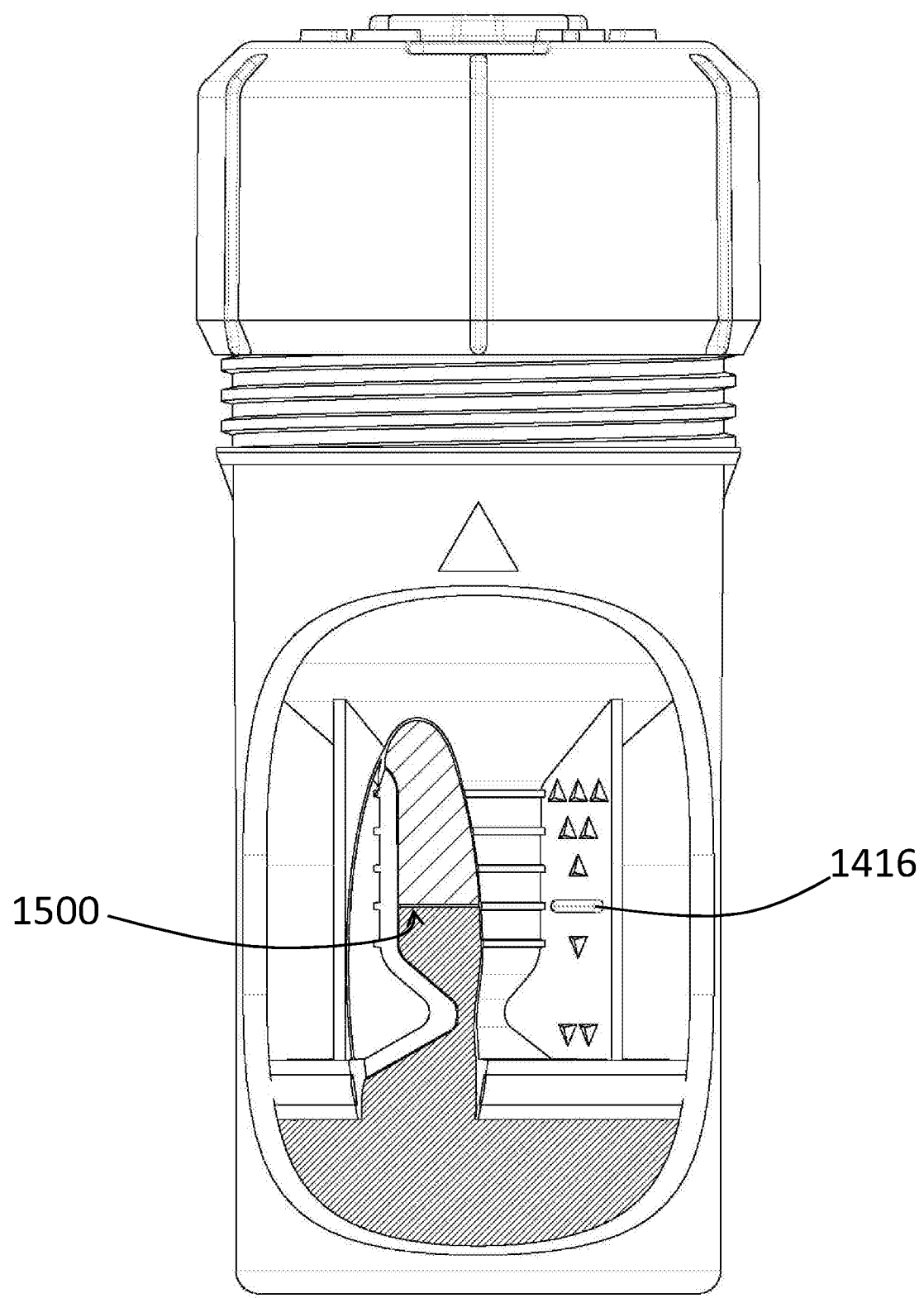

Continuing with the example, an initial centrifugation in step 1806 may result in the buffy coat layer 1500 position illustrated in FIG. 14, i.e. the buffy coat layer 1500 at the three upwardly-oriented triangles 1412. Upon identifying this position of the buffy coat layer 1500, the user is then instructed, by the corresponding measurement marking 1408, how many $1/6^{th}$ turns and in what direction the user should rotate the cap portion 702 in order to move the buffy coat layer 1500 to the optimum buffy coat position corresponding to the straight-line bar indicate 1416. Accordingly, in step 1808, the user may adjust the volume of the second cavity 808 by translating the first container body 800 relative to the second container body 802. Such translation is performed by rotating the cap portion 702 as indicated by the measurement marking 1408, which, in the case of FIG. 14, is by three (3) $1/6^{th}$ rotational turns of the cap portion 702 in a clockwise direction. Subsequently, in step 1810, the user may, after the rotational turns in step 1808, centrifuge the fluid biological product 1418 a second time in order to re-position the buffy coat layer 1500 to a second position, different than the first position of the buffy coat layer 1500. FIG. 17 illustrates the buffy coat layer 1500 at the optimum position at the straight-line bar indicator 1416. With the buffy coat layer 1500 at the optimum position, the user may utilize a syringe to extract the buffy coat layer 1500. Advantageously, the syringe may be of a predetermined length to specifically extract the buffy coat layer 1500 at the optimum position when the syringe is inserted into the entry/exit port 700. Because the buffy coat layer 1500 is extremely thin, having a predetermined length syringe can make extracting the buffy coat layer 1500 with a syringe much easier, without having to guess or "eye-ball" its position.

Figure 16:
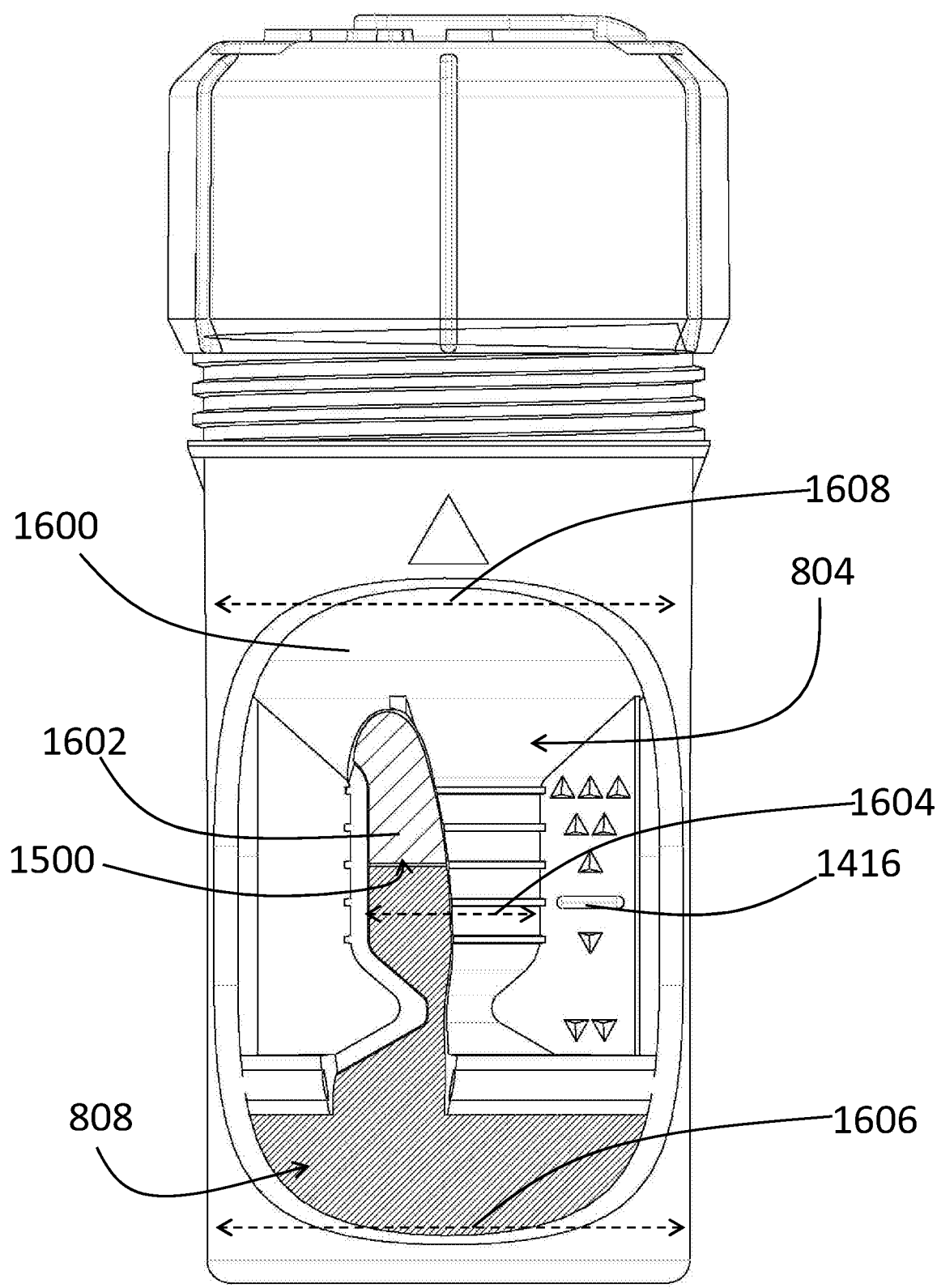

As yet another example, an initial centrifugation, in step 1806, may result in FIG. 16, showing the buffy coat layer 1500 corresponding to a single upwardly-oriented triangle 1412. Accordingly, in this example, the user is informed by the measurement markings 1408 to rotate the cap portion 702 one (1) $1/6^{th}$ turn in a clockwise direction in order to re-position the buffy coat layer 1500 to the optimum position. After the user rotates the cap portion 702 as such, a subsequent centrifugation, at step 1810, should result in the buffy coat layer 1500 being disposed at the straight-line bar indicator 1416.

It should be understood that in other embodiments, other marking configurations may used to instruct the user, but such marking configurations should still inform the user as to what actions to take to adjust the volume of the second cavity 808 in order to intentionally re-position the buffy coat layer 1500 at the optimum position.

In step 1812, with the buffy coat layer 1500 at the desired position, the user may use a needle or syringe to remove the plasma layer 1502 from the first cavity 804, via the entry/exit port 700, leaving the buffy coat layer 1500 and the red blood cell layer 1504 in the neck portion 1602 and the second cavity 808 portion. The needle or syringe may be of a predetermined configuration and size specifically designed for the user to remove the plasma layer 1502 from the first cavity 804.

In step 1814, with the plasma layer 1502 removed, the user may use a second need or syringe to resuspend the buffy coat layer 1500, which includes both white blood cells and platelets. The second needle or syringe may be of a predetermined configuration and size specifically designed for the user to remove the buffy coat layer 1500 in the neck portion 1602. With the plasma layer 1502 removed, the resuspended buffy coat layer 1500 and the overall remaining fluid biological product should be disposed in the lower, narrow portion of the cavities 804, 808, i.e., the neck portion 1602 and the second cavity 808.

In step 1816, the user may centrifuge the fluid biological product, including the resuspended buffy coat layer, in order to further separate the white blood cells and the platelets further. As a result of such centrifugation, the white blood cells and platelets should separate such that the white blood cells form a new buffy coat layer and the platelets remain in the plasma layer above the new buffy coat layer. Due to the disposition of the fluid biological product within the lower, narrow portion of the cavities 804, 808, i.e., the neck portion 1602, the user may centrifuge the product in step 1816 at a rotational speed that is less than the rotational speed used to centrifuge in steps 1806 and 1810. The narrow neck, in combination with slower rotational speeds utilizes the "wall effect" to separate white blood cells and platelets in the narrow neck portion 1602. Without the narrow neck portion 1602, the "wall effect" does not efficiently separate the cells. Advantageously, the narrow neck portion 1602 and lower centrifuge speeds provides for the ability to separate the white blood cells and platelets that cannot be performed efficiently in a wider cavity.

In step 1818, the user can use the needle or syringe to remove the new plasma layer with platelets, via the entry/exit port 700. This resulting plasma layer includes platelets and reduced white blood cells that can be very useful for situations where a low white blood cell count is desired. In addition, in step 1820, the user can resuspend the new buffy coat layer (similar to step 1816) in order to produce a buffy coat layer with a higher white blood cell count, with reduced platelets. As would be recognized by one of ordinary skill in the art, resuspension of the buffy coat layer and recentrifugation in the neck portion 1602 of the centrifugal separating assembly 600 as discussed herein allows the user to selectively adjust the white blood cell and platelet concentrations in discrete layers, as needed for different types of treatments. As discussed herein above in the background section, choosing the appropriate concentration of white blood cells for certain treatments can be an important aspect of a patient's successful recovery.

The process may end at step 1822.

A centrifugal separating assembly has been disclosed that can be placed in a centrifuge to separate a fluid product into discrete components according to varying weights of the discrete components.

What is claimed is:

1. A centrifugal separating assembly for separating a fluid biological product into discrete components by centrifugation, the assembly comprising:
a first container body at least partially defining a first cavity in fluid communication with a second cavity via a common inlet-outlet port;
a cap coupled to a top of the first container body, the cap having a threaded portion;
a second container body that is configured to receive at least a portion of the first container body therein such that the second container body forms at least one wall of the second cavity, the second container body having a threaded top portion, the first container body disposed to selectively translate relative to the second container body such that the at least one wall of the second cavity is selectively translated so as to selectively adjust a volume of the second cavity, wherein the first container body is selectively translated within the second container body by the threaded portion of the cap engaging the threaded top portion of the second container body, and wherein upon being so engaged rotating the cap moves the first container body within the second container body.

2. The centrifugal separating assembly in accordance with claim 1, further comprising:
a plurality of measurement markings on an outside surface of the first container body, each of the plurality of measurement markings disposed to indicate to a user one of a plurality of translation movements of the first container body relative to the second container body that corresponds to a selected predetermined position of a discrete layer of a fluid biological product within the first cavity, and
wherein the second container body is made of a transparent material.

3. The centrifugal separating assembly in accordance with claim 2, wherein:
the plurality of measurement markings correspond to an amount of rotation of the cap when the threaded portion of the cap is engaged with the threaded top portion of the second container body.

4. The centrifugal separating assembly in accordance with claim 1, wherein the first container body is transparent.

5. The centrifugal separating assembly in accordance with claim 1, wherein:
the first cavity includes a main cavity portion, a neck portion having a diameter that is less than a diameter of the main portion, and a common inlet-outlet port at a bottom of the neck portion between the neck portion and the second cavity.

6. The centrifugal separating assembly in accordance with claim 1, further comprising:
an entry port defined by the cap portion, the entry port adapted to introduce a fluid biological product into the first cavity.

7. The centrifugal separating assembly in accordance with claim 1, wherein:
the first container body is concentric with the second container body.

8. A method of separating a fluid biological product into discrete layers by centrifugation, the method comprising:
providing a centrifugal separating assembly including:
a first container body at least partially defining a first cavity in fluid communication with a second cavity via a common inlet-outlet port;
a cap coupled to a top of the first container body, the cap having a threaded portion;
a second container body being configured to receive at least a portion of the first container body therein such that the second container body forms at least one wall of the second cavity, the second container body having a threaded top portion, the first container body disposed to selectively translate relative to the second container body such that the at least one wall of the second cavity is selectively translated so as to selectively adjust a volume of the second cavity, wherein the first container body is selectively translated within the second container body by the threaded portion of the cap engaging the threaded top portion of the second container body, and wherein upon being so engaged rotating the cap moves the first container body within the second container body;
introducing the fluid biological product into the first cavity;
adjusting the cap
after introducing the fluid biological product, centrifuging the fluid biological product to separate the fluid biological product into discrete layers.

9. The method in accordance with claim 8, further comprising:
identifying a first position of a buffy coat layer, the buffy coat layer being one of the discrete layers of the fluid biological product.

10. The method in accordance with claim 9, further comprising:
after identifying the first position of the buffy coat layer, selectively translating the first container body relative to the second container body to selectively adjust a volume of the second cavity.

11. The method in accordance with claim 10, wherein:
wherein providing the centrifugal separating assembly includes providing the second container body being made of a transparent material; and selectively translating the first container body relative to the second container body includes rotating a cap portion of the first container body to position a marking on the first container body at a selected position.

12. The method in accordance with claim 10, further comprising:
after selectively translating the first container body relative to the second container body, centrifuging the fluid biological product to re-position the buffy coat layer to a second position different than the first position of the buffy coat layer.

13. The method in accordance with claim 12, wherein:
the second position of the buffy coat layer is based on the selectively adjusted volume of the second cavity.

14. The method in accordance with claim 8, wherein:
the discrete layers includes a plasma layer, a buffy coat layer, and a red blood cell layer.

15. The method in accordance with claim 8, wherein:
introducing the fluid biological product comprised introducing the fluid biological product into the first cavity through a port on a top of the cap.

16. The method in accordance with claim 8, further comprising:
before introducing the fluid biological product, inserting the first container body within the second container body such that the first container body is concentric with second container body.

17. A centrifugal separating assembly, comprising:
a first container body which defines first cavity at a top portion of the first container, the first cavity having a main cavity portion and a neck portion, the neck portion having a smaller diameter than a diameter of the main cavity portion, the neck portion being below the main cavity portion, a common inlet-outlet port being formed at a bottom of the neck portion;
a cap that is configured to attach to a top of the first container body, and which include a threaded portion that does not engage the first container body;
a second container body that is configured to receive the first container body therein, and to at least partially define a second cavity under the first container body, wherein the second cavity is fluidically connected to the first cavity through the common inlet-outlet port, the second container body being threaded at a top of the second container body with threads that are configured to engage the threaded portion of the cap; and
wherein rotating the cap adjusts a position of the first container body within the second container body to a selected position of a layer of a fluid biological product after centrifugation of the centrifugal separating assembly when containing the fluid biological product.

18. The centrifugal separating assembly of claim 17, wherein:
the second container body is transparent; and
the first container body comprises location markings on an outside of the first container body which indicate a position of the first container body within the second container body to facilitate movement of the first container body within the second container body to the selected position.

19. The centrifugal separating assembly of claim 18, wherein the first container body is transparent.

20. The centrifugal separating assembly of claim 17, wherein the cap comprises a port through which the fluid biological product is introduced into the centrifugal separating assembly.

* * * * *